(12) United States Patent
Zettl et al.

(10) Patent No.: US 7,915,973 B2
(45) Date of Patent: Mar. 29, 2011

(54) TUNABLE MULTIWALLED NANOTUBE RESONATOR

(75) Inventors: Alex K. Zettl, Kensington, CA (US); Kenneth J. Jensen, Berkeley, CA (US); Caglar Girit, Albany, CA (US); William E. Mickelson, San Francisco, CA (US); Jeffrey C. Grossman, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1244 days.

(21) Appl. No.: 11/467,422

(22) Filed: Aug. 25, 2006

(65) Prior Publication Data

US 2009/0309676 A1 Dec. 17, 2009

Related U.S. Application Data

(60) Provisional application No. 60/711,937, filed on Aug. 25, 2005.

(51) Int. Cl.
*H03H 9/24* (2006.01)
(52) U.S. Cl. .......................... 333/186; 333/197; 977/752
(58) Field of Classification Search .................. 977/752, 977/743, 724; 333/186, 197; 205/766, 768
See application file for complete search history.

(56) References Cited

U.S. PATENT DOCUMENTS

| | | | | |
|---|---|---|---|---|
| 6,803,840 | B2 * | 10/2004 | Hunt et al. | 333/186 |
| 7,053,520 | B2 * | 5/2006 | Zetti et al. | 310/309 |
| 7,238,425 | B2 * | 7/2007 | Cumings et al. | 428/403 |
| 7,382,648 | B2 * | 6/2008 | Bockrath | 365/164 |
| 7,569,941 | B2 * | 8/2009 | Majumdar et al. | 257/798 |
| 7,579,618 | B2 * | 8/2009 | Adam | 257/25 |
| 2007/0171707 | A1 * | 7/2007 | Maslov et al. | 365/185.01 |
| 2009/0212884 | A1 * | 8/2009 | Kaunisto et al. | 333/186 |
| 2009/0277609 | A1 * | 11/2009 | Chang et al. | 165/96 |

* cited by examiner

*Primary Examiner* — Benny Lee
*Assistant Examiner* — Alan Wong
(74) *Attorney, Agent, or Firm* — Leonard T. Guzman; Lawrence Berkeley National Laboratory

(57) ABSTRACT

A tunable nanoscale resonator has potential applications in precise mass, force, position, and frequency measurement. One embodiment of this device consists of a specially prepared multiwalled carbon nanotube (MWNT) suspended between a metal electrode and a mobile, piezoelectrically controlled contact. By harnessing a unique telescoping ability of MWNTs, one may controllably slide an inner nanotube core from its outer nanotube casing, effectively changing its length and thereby changing the tuning of its resonance frequency. Resonant energy transfer may be used with a nanoresonator to detect molecules at a specific target oscillation frequency, without the use of a chemical label, to provide label-free chemical species detection.

13 Claims, 5 Drawing Sheets

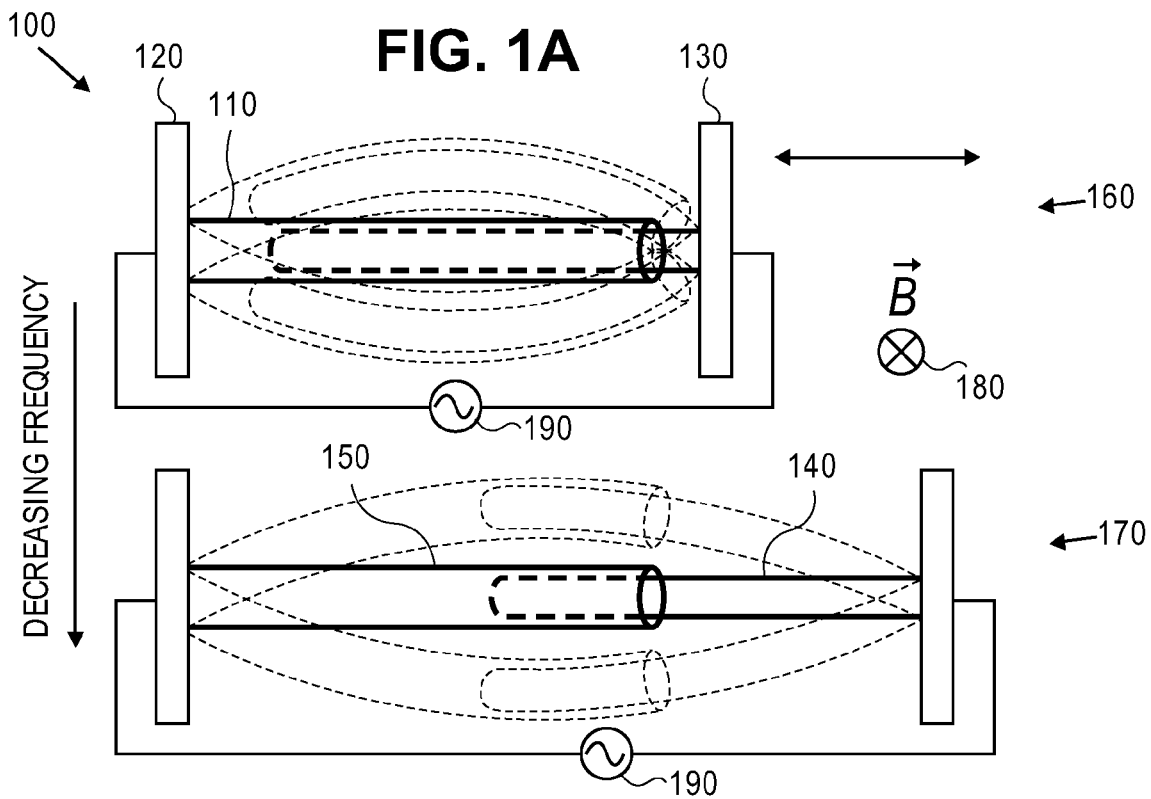

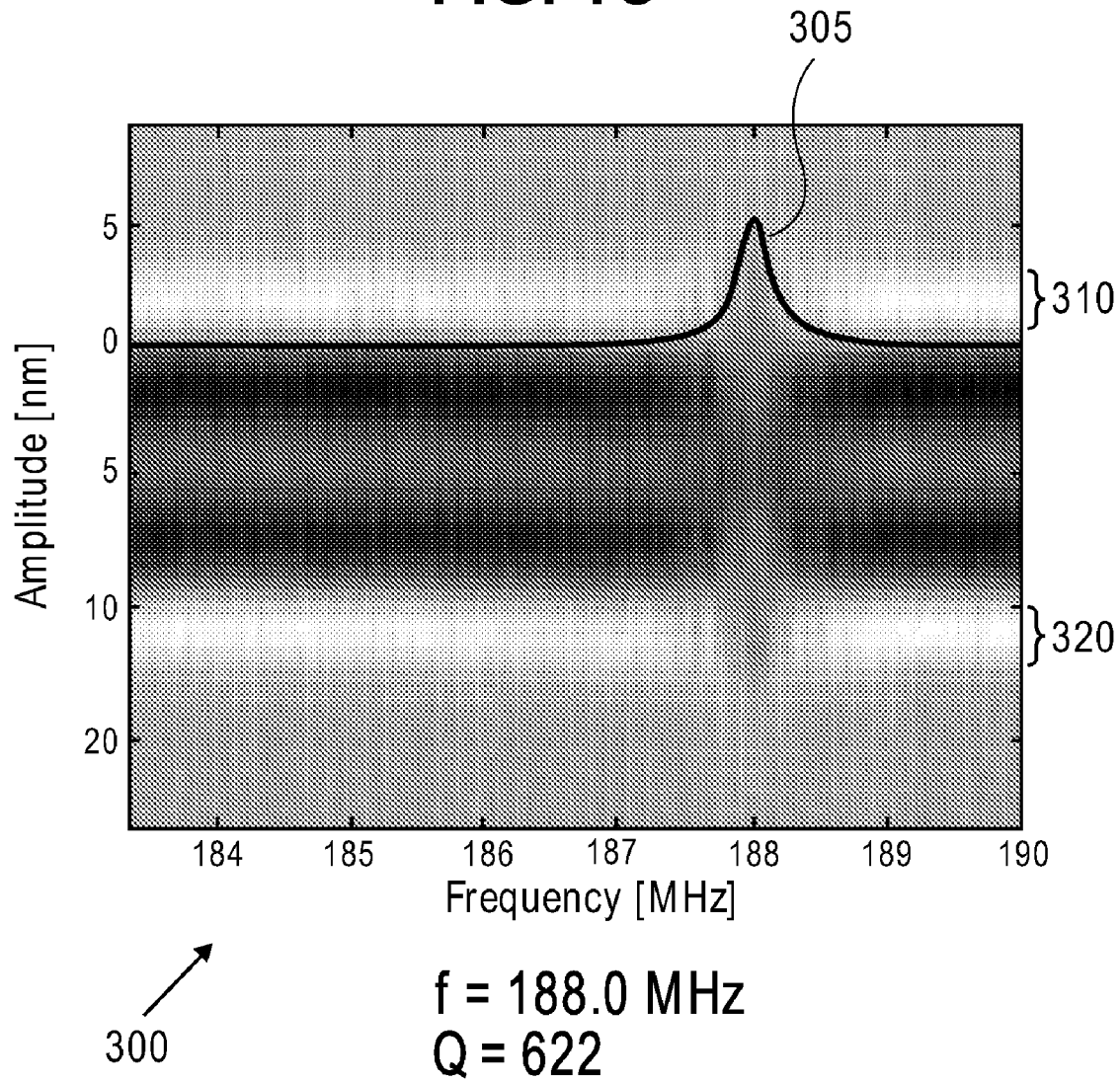

$f_0$ = 315 KHz
FUNDAMENTAL $f_1$ = 1.80 MHz
1st HARMONIC (PRIOR ART)

TUNABLE MULTIWALLED NANOTUBE RESONATOR

CROSS REFERENCE TO RELATED APPLICATIONS

This US patent application claims benefit of priority to U.S. provisional patent application 60/711,937 filed Aug. 25, 2005.

STATEMENT REGARDING FEDERAL FUNDING

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO A COMPUTER PROGRAM

Not Applicable.

BACKGROUND OF THE INVENTION

1. Field of the Invention

The present invention generally relates to resonating nanotubes, more specifically to resonant frequency tunable nanotubes, and still more specifically to resonant frequency tunable carbon multiwall nanotubes (MWNT).

2. Description of the Relevant Art

Nanoscale resonators, with their low masses, low force-deflection spring-rate constants, and high resonant frequencies, are capable of weighing single bacteria [ILIC 00], detecting single spins in magnetic resonance systems [RUGA 04], and even probing quantum mechanics in macroscopic systems [LAHA 04], [BRES 02]. These resonators are typically created from surface-micromachined silicon; however, carbon nanotubes provide an alternate, nearly ideal building material because of their low density, high Young's modulus, and atomically perfect structure. Already there has been much progress in analyzing and constructing nanotube-based resonators [LI 04], [SAZO 04].

Present designs typically either operate at a single frequency or have a relatively narrow frequency range, possibly imposing limitations in their application.

These resonators are typically micromachined from silicon; however, because of their low density, high Young's modulus, and atomically perfect structure, carbon nanotubes provide an alternate, nearly ideal building material. Some progress has been made in constructing nanotube-based resonators [SAZO 04]. However, these resonators have a narrow frequency range and obey a relatively complicated physical model.

U.S. Pat. No. 6,709,566, hereby incorporated by reference describes a method for shaping small three-dimensional articles such as nanotubes exhibiting a layered structure through material removal such that the article is controllably shaped to exhibit a desired contour. Typically, material removal does not require use of a chemical etchant and is carried out while the article and a shaping electrode are positioned in contact material removal relationship with under a potential difference. The invention also relates to nanotubes and small three-dimensional articles exhibiting a layered structure having a controllably shaped contour.

U.S. Pat. No. 6,803,840, hereby incorporated by reference describes a tunable nanomechanical oscillator device and system. The nanomechanical oscillator device comprises at least one nanoresonator, such as a suspended nanotube, designed such that injecting charge density into the tube (e.g. by applying a capacitively-coupled voltage bias) changes the resonant frequency of the nanotube, and where exposing the resonator to an RF bias induces oscillatory movement in the suspended portion of the nanotube, forming a nanoscale resonator, as well as a force sensor when operated in an inverse mode. A method of producing an oriented nanoscale resonator structure with integrated electrodes is also provided in the patent.

Here is proposed a fundamentally different nanotube resonator, which takes advantage of one of carbon nanotubes' most interesting properties. Multiwalled carbon nanotubes (MWNTs), which consist of multiple, concentric nanotubes precisely nested within one another, exhibit a striking telescoping property whereby an inner nanotube core may slide within the atomically smooth casing of an outer nanotube shell [CUMI 00a]. Already this property has been exploited to build a rotational nanomotor [FENN 03] and a nanorheostat [CUMI 04]. Future nanomachines such as a gigahertz mechanical oscillator are envisioned [ZHEN 02]. By harnessing this versatile telescoping property in a new fashion, a tunable nanoscale resonator has been developed.

BRIEF SUMMARY OF THE INVENTION

This invention provides an apparatus and applications for a tunable multiwalled nanotube. Such tunable nanotube is embodied here as a tunable multiwalled carbon nanotube resonator.

In one embodiment, a tunable resonator may comprising: a) an extendable multiwalled nanotube having two ends; and b) an extension means attached to each of the two ends of the extendable multiwalled nanotube; c) whereby the extension means displaces the two ends of the attached extendable multiwalled nanotube.

The tunable resonator above may further comprise: a) an excitation means, which may or may not act in conjunction with the extension means; b) which causes the extendable multiwalled nanotube to vibrate. One example of where the excitation means acts in conjunction with the extension means is where a current is passed first through the extension means, then through the resonator. When the resonator is subjected to a magnetic field, then the impressed current generates an excitation force on the resonator, causing it to vibrate. Similarly, when the resonator is subject to an electrostatic field, then an impressed voltage generates an excitation force on the resonator, causing it to vibrate These forces are due to standard electrostatic or electromagnetic forces generally described in first year college physics texts.

The tunable resonator above may have the excitation means comprising: a) an electromagnetic field disposed about the extendable multiwalled nanotube; and b) a variable current that passes through the extendable multiwalled nanotube, so as to cause a vibration in the extendable multiwalled nanotube.

The tunable resonator extendable multiwalled nanotube may comprise: a) a carbon multiwalled nanotube, comprising at least two walls. Additionally, a deflection sensor means may be provided that detects an amplitude of the extendable multiwalled nanotube deflection.

The extension means may generally be regarded as controlling the deflection of the resonator, which in conjunction with the excitation means, causes the resonator to vibrate. The extension means may be attached to one or both ends of the resonator. If attached to only one end, then the other end may be fixed, or attached to a different extension means operating in either the same, or a different manner of extension. Ultimately, the resonator is either lengthened or shortened through the action of the extension means, thus changing the resonator frequency of oscillation.

In another embodiment, a method for tunably resonating a multiwalled nanotube may comprise: a) disposing an extendable mount attaching to a multiwalled nanotube at both ends of the multiwalled nanotube; b) displacing the extendable mount to extend the attached multiwalled nanotube to a desired displacement; and c) exciting the multiwalled nanotube to cause it to vibrate. The method may further comprise: a) detecting an amplitude of the multiwalled nanotube vibration. Again, the multiwalled nanotube may be a carbon multiwalled nanotube.

The methods above may use the exciting step comprised of: a) passing a current through the multiwalled nanotube; and b) providing an electromagnetic field disposed about the multiwalled nanotube.

The methods above may further comprise: a) controlling the desired displacement so that the amplitude of the multiwalled nanotube vibration is maximized at a central resonant frequency; and b) measuring a frequency of the multiwalled nanotube vibration.

In another embodiment, the methods above may further comprise: a) reducing a particle number density of a dissipative fluid disposed about the multiwalled nanotube to increase the Q of the multiwalled nanotube. The fluid may be atomic or molecular, and may be in gaseous or liquid form, or any mixture of the preceding.

In still another embodiment, the methods above may further comprise: a) calculating a change in length of the multiwalled nanotube through a change in the central resonant frequency between a first and second value of the desired displacement.

In another embodiment, a method for measuring force by tunably resonating a multiwalled nanotube may comprise: a) disposing an extendable mount attaching to a multiwalled nanotube at one end of the multiwalled nanotube; b) detecting an amplitude displacement of the multiwalled nanotube vibration; c) exciting the multiwalled nanotube to cause it to vibrate; d) controlling the desired amplitude displacement so that the amplitude of the multiwalled nanotube vibration is maximized at a central resonant frequency; and e) measuring a frequency of the multiwalled nanotube vibration. Again, the multiwalled nanotube may be a carbon multiwalled nanotube. Additionally, the exciting step may comprise: a) passing a current through the multiwalled nanotube; and b) providing an electromagnetic field disposed about the multiwalled nanotube.

Alternatively, electrostatic operation may be obtained by placing a charged voltage on the resonator in the presence of an electric field, thereby producing Coulomb forces and thus driving the resonator to oscillate.

In another embodiment, one may add still more steps, comprising: a) applying a force to the extendable mount, resulting in a change in length of the multiwalled nanotube with a consequent change in central resonant frequency; b) calculating the magnitude of the force applied to the extendable mount by the consequent change in central resonant frequency. In this embodiment, the applying a force step may comprise: a) applying a mass in a gravitational or accelerating field to generate the force.

In still another embodiment, a label free tunable nanoresonator detector is made, comprising: a tunable nanoresonator without a chemical label; a tuning means, whereby the nanoresonator is tuned to a specific target oscillation frequency; and a detector means; whereby a specific target molecule is detected by the nanoresonator. In this device, the tuning means may be any of the above methods of effecting a change in length of the tunable nanoresonator. Detection may be made either passively, where detection of oscillation of the nanoresonator tuned to a target detection frequency is observed, or actively, when driven oscillation of the tunable resonator at the target detection frequency results in a change in amplitude of the oscillations, indicating the presence of the target molecule vibration. In this device a specific chemical label sensor is not required, as the molecular vibration is directly detected without any bonding of the molecule to the tunable nanoresonator.

In another embodiment, a method of label free tunable nanoresonator detection is disclosed, comprising: providing a tunable nanoresonator without a chemical label; tuning the nanoresonator to a specific target oscillation frequency; and means for detecting a specific target molecule by a resonant energy transfer with the nanoresonator. These details, and the means for detecting, are described above.

BRIEF DESCRIPTION OF THE SEVERAL VIEWS OF THE DRAWINGS

The invention will be more fully understood by reference to the following drawings, which are for illustrative purposes only:

FIG. 1A is a schematic of a tunable nanoresonator.

FIG. 1B is a drawn representation of a photomicrograph (in this instance, from a transmission electron microscope) of a tunable nanoresonator device in action.

FIG. 1C shows composite image of line profiles of a nanotube during a frequency sweep through resonance.

DETAILED DESCRIPTION OF THE PREFERRED EMBODIMENT

Definitions

Figure 2A:
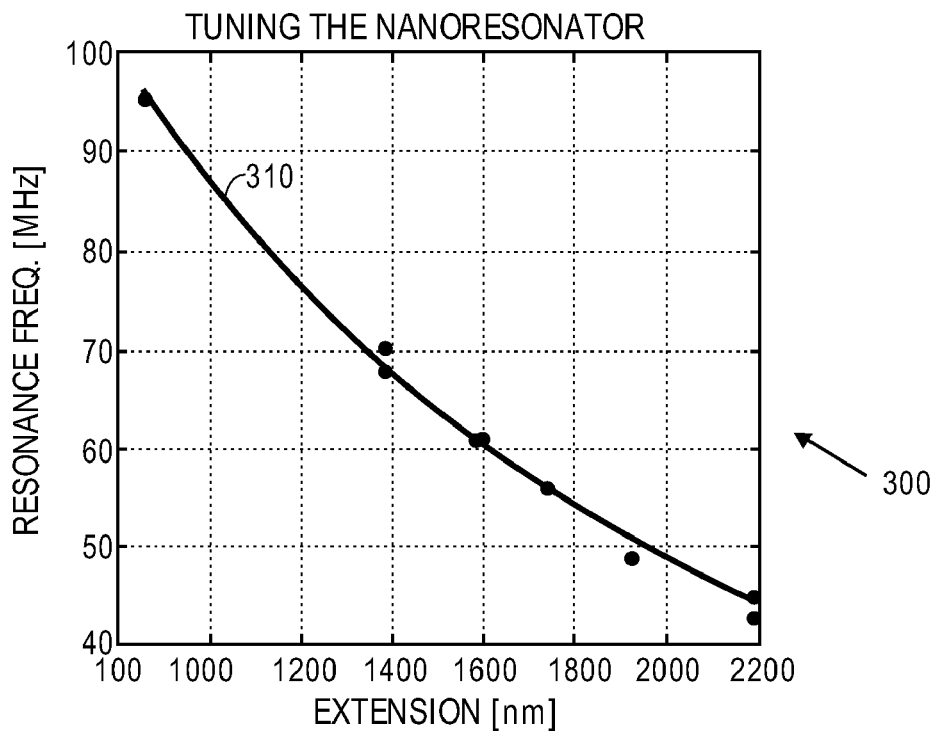
FIG. 2A is a graph plotting frequency (in MHz) versus extension (in nm), which demonstrates the tuning process. The data follow $1/L^2$ the dependence expected from the Euler-Bernoulli resonance equation.

Nanotube as used herein refers to a solid, cylindrically shaped, and discrete fibril typically characterized by a substantially constant diameter of typically about 1 nm to about 100 nm, preferably about 2 nm to about 50 nm. In addition, the nanotube typically exhibits a length greater than about 10 times the diameter, preferably greater than about 100 times the diameter.

Multiwalled nanotube (MWNT) refers to nanotubes having a layered structure, such as a fullerene-like structure, so that the nanotube comprises an outer region of multiple continuous layers of ordered atoms and an optional distinct inner core region or lumen. The layers are disposed substantially concentrically about the cylindrical axis of the fibril. One example of a MWNT is a carbon MWNT.

Resonator as used herein refers to an extendable MWNT that is use as a vibrating mechanical oscillator.

Introduction

FIG. 1A is a schematic drawing of a tunable nanoresonator 100. A MWNT 110 is suspended between a metal electrode 120 and a mobile, piezoelectrically controlled contact 130. By peeling the outer shell of the MWNT [CUMI 00b] and exposing the inner core of the MWNT, one may harness its unique telescoping ability. Like a trombone player shifting notes, one may controllably slide the inner nanotube 140 from its casing 150 using the mobile contact, effectively changing the length of the MWNT and thereby tuning its resonant frequency. In the top image 160 of FIG. 1A, the resonator is fully retracted and has a relatively high resonant frequency. In the bottom image 170 of FIG. 1A, the resonator is extended and consequently has a lower resonant frequency. By operating the device in an external magnetic field 180 and applying alternating current 190, one may excite the mechanical vibrations of the nanotube via the Lorentz force [CLEL 96]. With a transmission electron microscope (TEM) it is possible to detect these vibrations through the physical displacement of the beam.

As described previously, the resonator may be operated by Coulomb forces in an electrostatic field (not shown in the Figures).

Sketched outlines obtained from transmission electron micrographs in FIG. 1B show a tunable nanoresonator in action. The first two images 210 and 220 show the nanotube beam at one extension before resonance (sharp) 210 and during resonance 220 at 225 MHz (blurred). The final two images 230 and 240 show the nanotube beam after the inner nanotube has been telescoped out 50 nm 230 prior to resonance. The resonance frequency has shifted downward to 193 MHz 240.

Resonance peaks are detected by analyzing video from the TEM with an image processing routine. For each video frame in a rectangular region such as 250, an image such as the one sketched in FIG. 1B is averaged along the length of the nanotube to provide a single time-slice representing the state of the nanotube. These slices, when combined, form a composite image 300, FIG. 1C, showing the amplitude of resonance as a function of time, or because frequency is ramped linearly, as a function of frequency. A Lorentzian fit 305 to the maximum (white) values 310 and 320 of the image gives values for the resonant frequency and quality factor, Q. FIG. 1C shows a typical resonance-response of an experimental nanoresonator.

Analysis of a Nanoresonator

The resonance frequency of the tunable nanoresonator obeys the Euler-Bernoulli beam equation, which makes explicit the dependence of the resonance frequency on the total length of the tube. The nanotube beam is treated as a continuum, elastic medium subject to the differential equation:

$$\frac{\partial^2}{\partial x^2}\left(EI\frac{\partial^2 y}{\partial x^2}\right) - \frac{\partial}{\partial x}\left(T\frac{\partial y}{\partial x}\right) = -\rho A\frac{\partial^2 y}{\partial t^2}$$

where y(x) is the transverse displacement of the beam along its length, x is the position along the length of the beam, E is the Young's modulus, I is the areal moment of inertia, T is the tension, $\rho$ is the density, t is time, and A is the cross-sectional area [SOUT 69]. For a cylindrical beam with outer and inner radii, $r_{outer}$ and $r_{inner}$, $I=\pi(r_{outer}^4 - r_{inner}^4)/4$. Though strictly speaking, the MWNT device is not a simple cylindrical beam, but rather a combination of two cylindrical beams, the outer shell nanotube and the inner core nanotube, and moreover its geometry changes during operation.

To simplify analysis of the nanoresonator, however, it is modeled as simple cylindrical beam with effective values of E, I, $\rho$, T, l, A, $r_{outer}$, and $r_{inner}$ which remain constant over the length of the beam and during operation. Applying the boundary conditions of a doubly-clamped system with beam length, l, (y(0)=0, y'(0)=0, y(l)=0, y'(l)=0) and solving the equation for the resonant frequency at the fundamental mode gives [SOUT 69]:

$$f_0 \approx \frac{22.4}{2\pi l^2} \frac{\sqrt{EI + 0.024Tl^2}}{\rho A},$$

where $r_{outer}$ is the effective radius of the outer wall of the nanotube system, $r_{inner}$ is the effective radius of the inner core of the nanotube system, E is the Young's modulus, and $\rho$ is the density. Effective radii are used to account for the fact that the actual radii are not constant across the length of the nanotube and change during telescoping. Numerical solutions for the fundamental mode frequency formula above using more complex two-cylinder and MWNT bundle models indicate that this approximate solution is accurate to within five percent for typical devices over their entire range of operation Tension in this device is supplied by the van der Waals attraction between the core nanotube and its shell, $F_{vdW}$=(0.2 J/m²)·C, where C is the core nanotube's circumference [CUMI 00a]. Interestingly, as a result, tension remains constant regardless of extension, temperature, or other environmental factors, allowing robust and reproducible results.

At the cost of increased complexity, the precise operation of the vibrating MWNT may be modeled, taking into account the stiffness of the mounting locations, the varying dimensions of the plurality of walls, and their disposition of length. For even more complexity, the nonlinear effects of high amplitude vibrations may be modeled, although such a model may no longer use a simple constant EI in the model, and instead use an EI(x,y) that is a function of spatial coordinates (x,y).

Experimental Results

As a demonstration of the ability to tune the resonator, in FIG. 2A appears a plot 300 of the resonance frequency versus extension length for a typical nanoresonator. The resonance frequency follows a predicted $1/L^2$ dependence. Moreover, from a curve fit 310 may be used to calculate the Young's modulus of a MWNT to be approximately 1.2 TPa, which appears to be in agreement with accepted values [PONC 99]. Also apparent in the graph is the extreme sensitivity of the resonance frequency to the extension length; 100 nm corresponds to a 5 MHz shift. Some other tunable resonator devices have shown sensitivities as great as 1 nm per 1 MHz shift. The extreme sensitivity of resonance frequency to the length of the beam suggests possible application as a nanoscale positioning device or an extremely sensitive strain gauge.

Figure 2B:
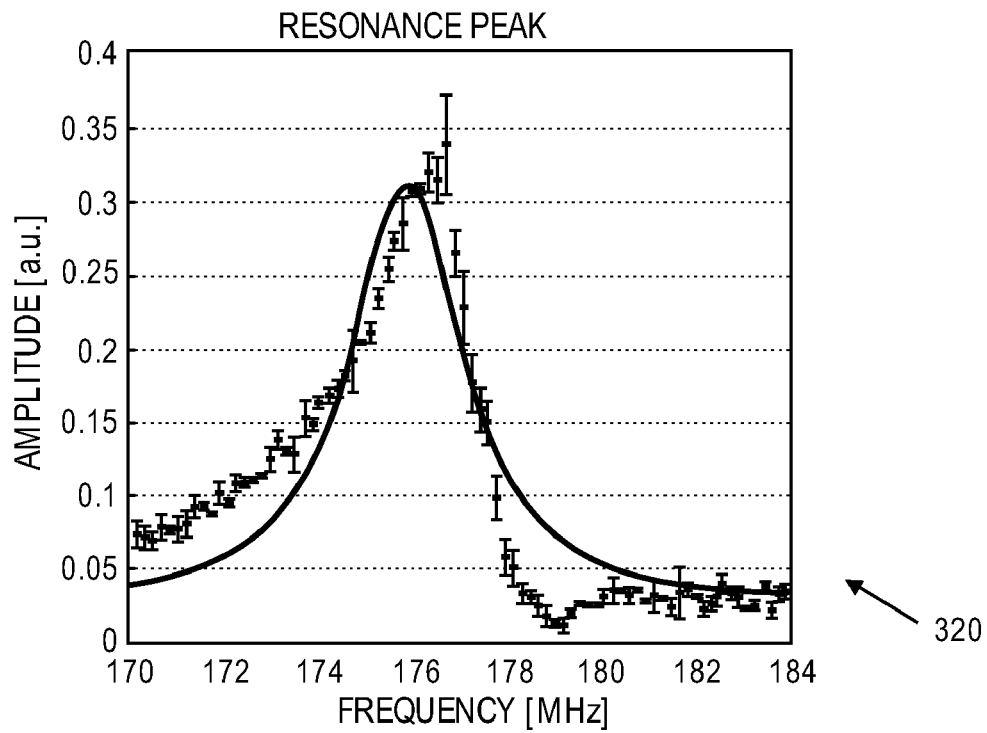
FIG. 2B is a graph of a typical resonance peak with amplitude (in arbitrary units) versus frequency (in MHz).

FIG. 2B shows a typical resonance peak that was observed by sweeping frequencies while maintaining the same extension 320. Current detection techniques require that the resonator be driven at large amplitudes, likely in the non-linear oscillation regime. This could explain the relatively low quality factor (Q=244) and the odd shape of the resonance peak. Magnetomotive detection [CLEL 96] should allow for smaller amplitudes, which may increase the quality factor. Note that non-linear oscillation is when small angle approximations such as $\sin(\theta) \approx \theta$ no longer remains approximately correct.

Figure 3A:
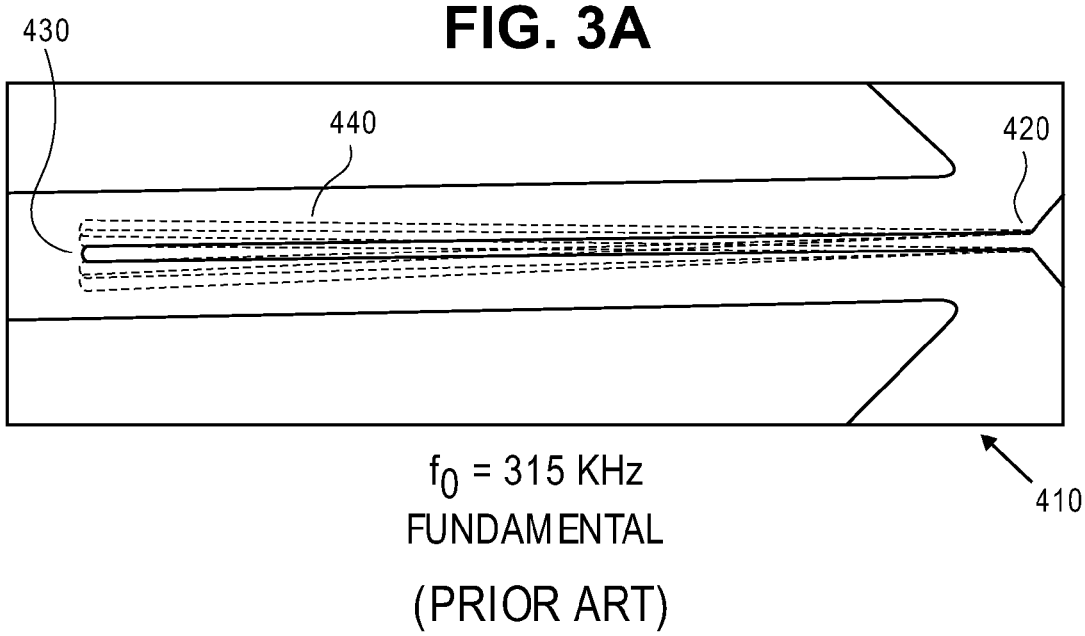
FIG. 3A is a drawn representation of a prior art electron micrograph of a single end mounted carbon nanotube of a fixed length vibrating at its fundamental frequency of 315 kHz.

FIG. 3A is a drawn representation of a prior art electron micrograph of a single end mounted 410 carbon nanotube fixed at one end 420 vibrating at its fundamental frequency of 315 kHz. The other end 430 is free to vibrate. This resonator is oscillating at its fundamental, lowest mode 440.

Figure 3B:
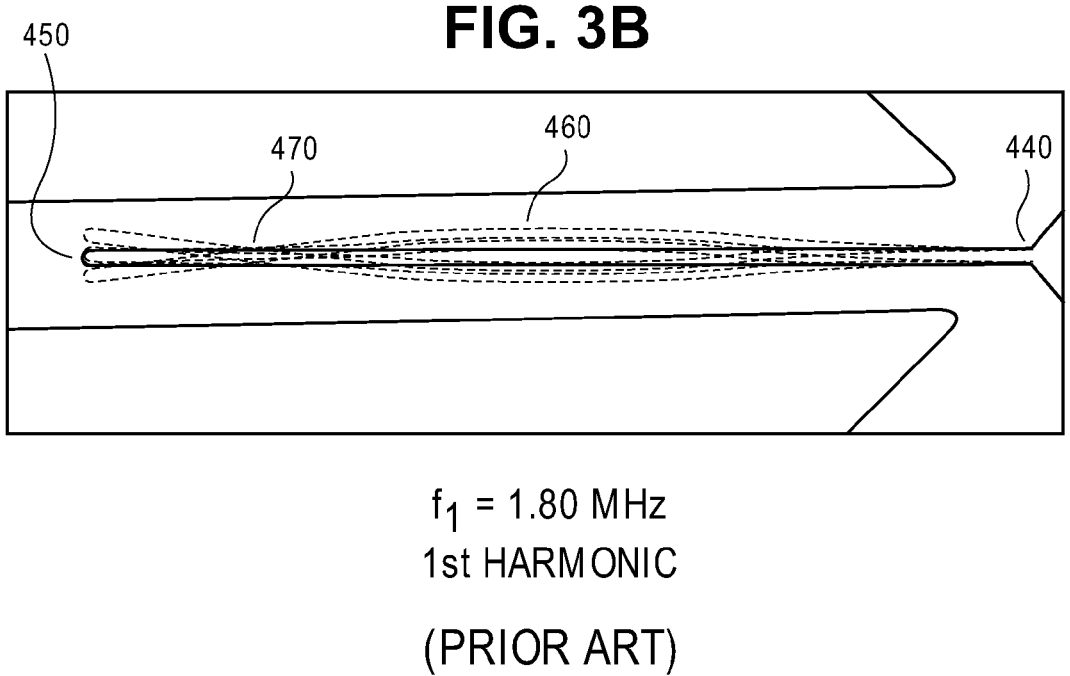
FIG. 3B is a drawn representation of a prior art electron micrograph of a single end mounted carbon nanotube of a fixed length vibrating at its first harmonic frequency of 1.80 MHz.

FIG. 3B is a drawn representation of a prior art electron micrograph of a single end mounted carbon nanotube identical to that of FIG. 3A of the same fixed length vibrating at its first harmonic frequency of 1.80 MHz. Here, the fixed end 440 is mechanically rigid compared to the nanotube, and the other end 450 is free to vibrate. The harmonic resonance envelope 460 shows that there is one point of zero amplitude 470 down the length of the nanotube besides the fixed end 440.

Figure 4A:
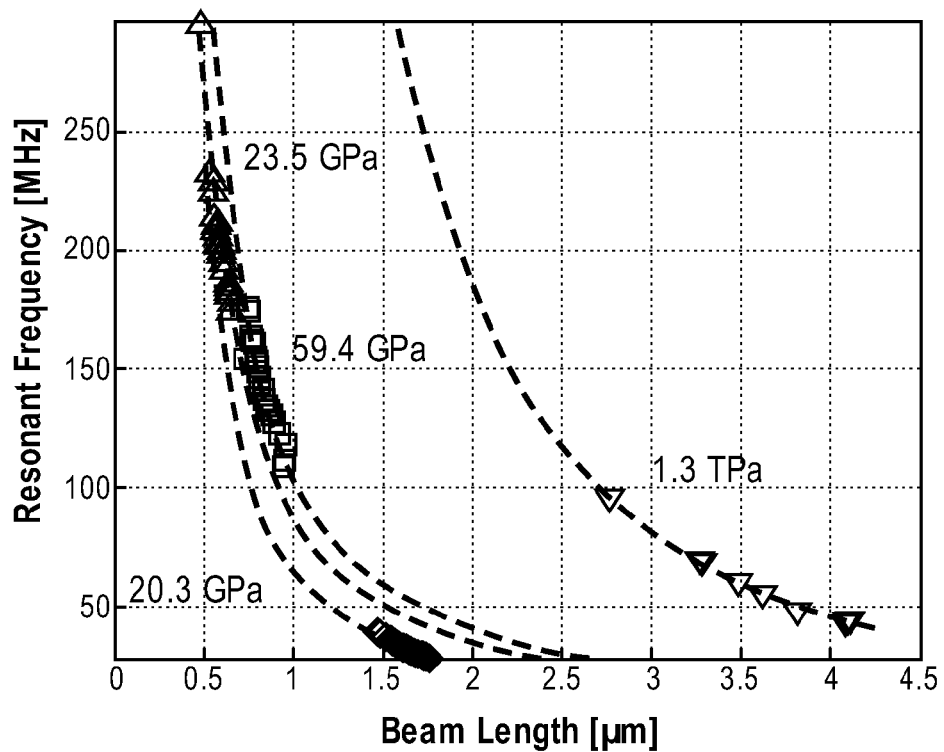
FIG. 4A shows typical tuning curves for four nanoresonator devices.

To demonstrate an ability to tune the nanoresonator, a plot of resonant frequency versus beam extension for four devices is shown in FIG. 4A. As expected, extended nanotubes produce lower frequencies as shown by all of the plotted lines. Also, each device covers a relatively wide range of frequencies, and together the devices span nearly the entire spectrum from 30 MHz to 300 MHz. Apparent in the graph is the extreme sensitivity of resonant frequency to beam extension, more than 1 MHz/nm for one device, suggesting possible application as a precision distance sensor or strain gauge.

Figure 4B:
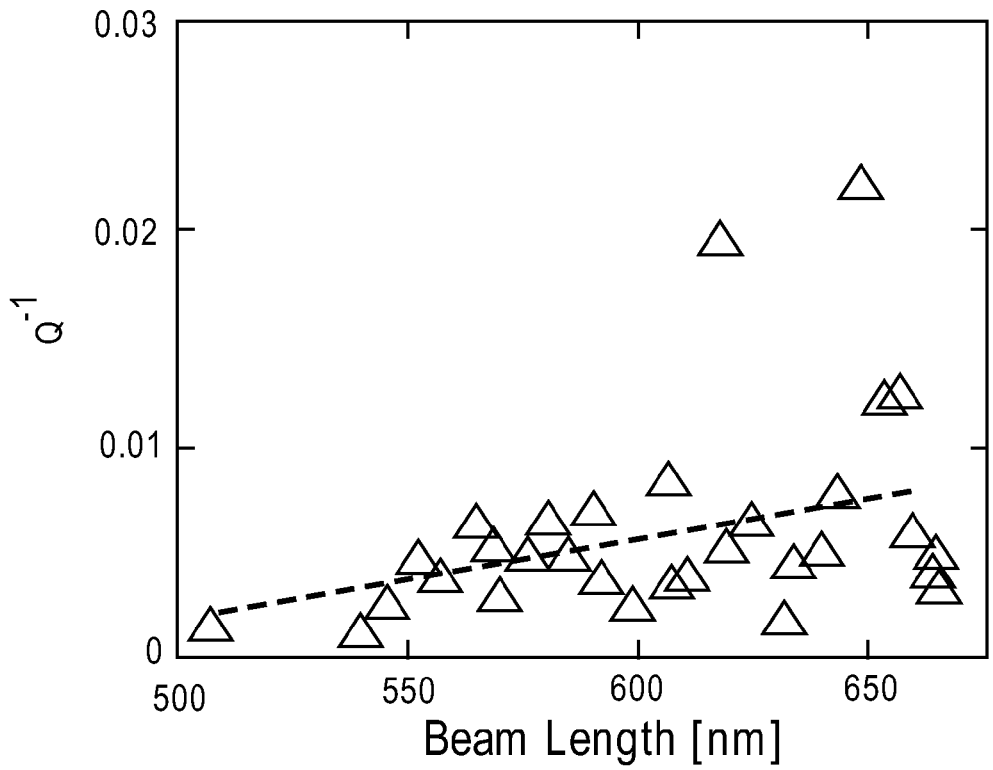
FIG. 4B shows typical 1/Q data points for the four nanoresonator devices of FIG. 4A at various lengths.

In FIG. 4B, one finds a plot of inverse quality factors versus beam length in nm. One sees that these inverse quality factors are generally less than 0.01, implying a Q of greater than 100—a fairly high quality factor for a mechanical resonator.

The measured maximum transverse displacement of these devices as a function of position is consistent with that of a doubly-clamped beam vibrating in its fundamental mode. Using the equation above to calculate $f_0$, one may fit curves to the experimental tuning data in FIG. 4A. Only the Young's modulus and an offset to the length of the beam were used as fitting parameters. Due to current fabrication technique limitations, some of the manufactured tunable nanoresonators are composed of nanotube bundles rather than individual nanotubes resulting in lower values for the effective Young's modulus, which may vary from one device to an-other. Also, the exact location of the sample-side clamp is often obscured in transmission electron microscope (TEM) imaging requiring the usage of a length offset. Specifically, here the change in length of the beam and determine the total length through the fitting parameter is directly measured. The plots in FIG. 4A show frequency versus the entire fitted length. The data follow the curves well and give reasonable values for the Young's modulus of a MWNT (1.3 TPa) [PONC 99] or MWNT bundles (20 GPa, 24 GPa, and 59 GPa) [DALT 03].

Nanoresonator Dissipation

As well as having many practical applications, the tunable resonator also provides an excellent platform for studying the physics of dissipation. FIG. 4B is a plot of energy dissipation ($Q^{-1}$) as a function of extension for one device. Note that both Q and $Q^{-1}$ are pure numbers, with no units associated with them. There appears to be a significant (p-value=0.03) positive correlation between dissipation and extension.

Possible dissipation mechanisms include eddy current damping, clamping loss, thermoelastic effects, core-shell sliding friction, and various irreversible processes involving surface defects and adsorbents. Eddy current damping [CLEL 99], though it would exhibit a positive correlation with extension, cannot account for the magnitude of the increase in dissipation. Clamping loss and thermoelastic dissipation both have a frequency dependence that would cause dissipation to decrease as length increases, opposite to what is observed. [BRAG 85] Moreover, thermoelastic dissipation is likely greatly suppressed because the nanotube may telescope to increase its length rather than stretch. Sliding friction could depend on overlap length between the core nanotube and shell nanotube; however again, dissipation would likely decrease with increased extension because there would be less overlap. [PERS 00] Surface losses therefore remain the most likely candidate for the dominant form of dissipation here. This important size-dependent contributor to dissipation has been suspected in other nanoscale oscillators [YASU 00].

Surface losses are typically modeled through the addition of a thin dissipative layer to the resonator's surface. Though our experiments were conducted in high vacuum ($10^{-7}$ Torr), the surface of the nanotube, even the newly exposed portion following telescoping, is likely covered with more than a monolayer of adsorbents, which functions as the dissipative layer. Dissipation, defined as the inverse of the quality factor, is given by: $Q^{-1} = \Delta W / W_0$, where $\Delta W$ is the energy lost per cycle and $W_0$ is the energy originally stored in the resonator. Stored energy is related to total resonator volume while energy lost per cycle is related to the volume of the dissipative surface layer, resulting in dissipation proportional to the surface-to-volume ratio. Thus, in most nanoscale resonators, dissipation is inversely proportional to length. [MOHA 02] Curiously, in the nanoresonator tested here, the actual volume of the resonator remains constant during extension giving a dissipation that is directly proportional to length, $Q^{-1} \alpha \alpha S / V \alpha L$.

The unique high-Q tunable nanoresonator shown here exhibits promise as a precise mass, force, position, or frequency sensor. It has demonstrated a wider frequency range than competing tunable nanoresonator designs. Also, its unique sliding ability lends itself to position sensing applications unlike other immobile resonators. Finally, its nearly perfect atomic structure and precisely controlled geometry make it an ideal tool to study the physics of dissipation.

By harnessing the almost frictionless sliding in telescoping MWNTs, a fundamentally new breed of tunable nanoscale resonator has been created. This resonator is unique in that it is the only known nanoresonator tunable via an effective length change, which suggests various nanoscale positioning or strain measurement applications. Also because the frequency follows a $1/L^2$ dependence, this resonator has a relatively wide frequency range compared to other tunable resonators. These advantages make this tunable nanoresonator an interesting candidate for further study and directed applications. In particular, the ability to tune to specific oscillation frequencies allows the tunable nanoresonator to readily transfer resonance energy from specific vibrational modes of certain target molecules, as further described below.

Resonant Energy Transfer and Label-Free Chemical Detection

By operating a nanoresonator at a constant, specific, frequency it is possible to detect resonant energy transfer between the nanoresonator and a target molecule. The chemical bonds within a given molecule give rise to high frequency oscillations between the atomic constituents in the molecule. Further, specific chemical groups of atoms have their own chemical resonant frequencies. Thus, for a particular chemical group, or for a specific molecule, it may be possible to choose a specific oscillatory target frequency that is unique to the target molecule. Then, detection of resonant energy transfer between a properly tuned nanoresonator and the target molecule, it is possible to detect the presence of the target molecule. Such detection would be practiced without the need for specific chemical labels, and hence would be label-free.

There are two broad methods thought for achieving such resonant energy transfer detection. A first method would be to have a nanoresonator tuned to the particular target frequency, and then to detect the onset of oscillations in the nanoresonator. Such onset would be indicative of chemical bonds vibrating at the target frequency, and would thereby indicate the presence of the target molecule. Second, the nanoresonator could be oscillated at the target frequency, and diminution of the amplitude of oscillation would indicate the presence of the target molecule.

Similarly, the two methods above could be used to detect certain target chemical groups common to many molecules by resonant energy transfer of vibrations at resonant frequencies common to the target chemical group.

Ideally, both the fundamental mode of the nanoresonator and the fundamental mode of the target oscillation would be the same, thereby not introducing any aliasing issues with modal overlap. Certainly, in the simplest implementation, both fundamental frequencies would be the same.

In yet another embodiment, the nanoresonator could be frequency swept, so as to detect multiple peaks of chemical vibrational modes, much as a swept frequency generator could be used to detect resonances and transfer functions in analog electrical circuits.

In any of the embodiments above, it would appear that there is no linking chemical bond required to detect target molecules. Thus, "label free" detection would be possible. This means that a single detection system may be used to detect many different molecules without the need for a new chemical functionalization (or labeling) of the detector. Since the detector is "label free", in theory continuous measurements may be made without cleaning, resetting, or degrading the sensor.

Such a type of detector system would appear to be one of the most important challenges to sensing. Since the detector system described here could detect virtually anything, it can be directly compared with other detection devices that have been modified to detect only a single molecular species. The results possible here would be obtainable much more efficiently because only one detector would be all that would be needed for all species, as opposed to a new detector for each and every species.

REFERENCES

The following references are referred to in the text of the specification above with brackets [xxxx nnL] referring to reference "xxxx nnL".

[BRAG 85] Braginski D, V. B., et al., *Systems with small dissipation*. 1985, Chicago: University of Chicago Press. xii, 145.

[BRES 02] Bressi, G., et al., *Measurement of the Casimir-force between parallel metallic surfaces*. Physical Review Letters, 2002. 88(4).

[CLEL 96] Cleland, A. N. and M. L. Roulces, *Fabrication of high frequency nanometer scale mechanical resonators from bulk Si crystals*. Applied Physics Letters, 1996. 69(18): p. 2653-2655.

[CLEL 99] Cleland, A. N. and M. L. Roukes, *External control of dissipation in a nanometer-scale radiofrequency mechanical resonator*, Sensors and Actuators a-Physical, 1999. 72: p. 256-261.

[CRAI 00] Craighead, H. G., *Nanoelectromechanical systems*. Science, 2000. 290(5496): p. 1532-1535.

[CUMI 00a] Cumings, J. and A. Zettl, *Low-friction nanoscale linear bearing realized from multiwall carbon nanotubes*. Science, 2000. 289(5479): p. 602-604.

[CUMI 00b] Cumings, J., P. G. Collins, and A. Zettl, *Materials—Peeling and sharpening multiwall nanotubes*. Nature, 2000. 406(6796): p. 586-586.

[CUMI 04] Cumings, J. and A. Zettl, *Localization and nonlinear resistance in telescopically extended nanotubes*. Physical Review Letters, 2004. 93(8).

[DALT 03] Dalton, A. B., et al., *Super-tough carbon-nanotube fibres—These extraordinary composite fibres can be woven into electronic textiles*. Nature, 2003. 423(6941): p. 703-703.

[FENN 03] Fennimore, A. M., et al., *Rotational actuators based on carbon nanotubes*. Nature, 2003. 424(6947): p. 408-410.

[ILIC 00] Ilic, B., et al., *Mechanical resonant immunospecific biological detector*. Applied Physics Letters, 2000. 77(3): p. 450-452.

[LAHA 04] LaHaye, M. D., et al., *Approaching the quantum limit of a nanomechanical resonator*. Science, 2004. 304(5667): p. 74-77.

[LI 04] Li, C. and T.-W. Chou, *Mass detection using carbon nanotube-based nanomechanical resonators*. Applied Physics Letters, 2004. 84(25): p. 5246-5248.

[MOHA 02] Mohanty, P., et al., *Intrinsic dissipation in high-frequency micromechanical resonators*. Physical Review B, 2002. 66(8).

[PERS 00] Persson, B. N. J., *Sliding friction: physical principles and applications*. 2nd ed. Nanoscience and technology, 2000, Berlin; New York: Springer. xi, 515.

[PONC 99] Poncharal, P., et al., *Electrostatic deflections and electromechanical resonances of carbon nanotubes*. Science, 1999. 283(5407): p. 1513-1516.

[RUGA 04] Rugar, D., et al., *Single spin detection by magnetic resonance force microscopy*. Nature, 2004. 430(6997): p. 329-332.

[SAZO 04] Sazonova, V., et al., *A tunable carbon nanotube electromechanical oscillator*. Nature, 2004. 431(7006): p. 284-287.

[SOUT 69] Southwell, R. V., *An introduction to the theory of elasticity for engineers and physicists*. 1969, New York: Dover Publications. vi, 509 p.

[YASU 00] Yasumura, K. Y., et al., *Quality factors in micron- and submicron-thick cantilevers*. Journal of Microelectromechanical Systems, 2000. 9(1): p. 117-125.

[ZHEN 02] Zheng, Q. S. and Q. Jiang, *Multiwalled carbon nanotubes as gigahertz oscillators*. Physical Review Letters, 2002. 88(4).

CONCLUSION

All publications, patents, and patent applications mentioned in this specification are herein incorporated by reference to the same extent as if each individual publication or patent application were each specifically and individually indicated to be incorporated by reference.

The description given here, and best modes of operation of the invention, are not intended to limit the scope of the invention. Many modifications, alternative constructions, and equivalents may be employed without departing from the scope and spirit of the invention.

We claim:

1. A tunable resonator, comprising:
   a) an extendable multiwalled nanotube having two ends; and
   b) an extension means attached to the two ends of the extendable multiwalled nanotube;
   c) whereby the extension means relatively displaces the two ends of the attached extendable multiwalled nanotube.

2. The tunable resonator of claim 1 further comprising:
   a) an excitation means;
   b) which causes the extendable multiwalled nanotube to vibrate.

3. The tunable resonator of claim 2, wherein the excitation means comprises:
   a) an electromagnetic field source that is configured to provide an electromagnetic field about at least part of the extendable multiwalled nanotube; and
   b) a variable current source that is configured to pass a variable electric current through the extendable multiwalled nanotube, so as to cause the extendable multiwalled nanotube to vibrate.

4. The tunable resonator of claim 1, wherein the extendable multiwalled nanotube comprises:
   a) a carbon multiwalled nanotube, comprising at least two walls.

5. The tunable resonator of claim 1, further comprising:
   a) a deflection sensor means that detects an amplitude of deflection in the extendable multiwalled nanotube.

6. The tunable resonator of claim 1, wherein the extension means comprises:
   a) a fixed attachment that rigidly attaches the extendable multiwalled nanotube to one of the two ends; and
   b) an extension attachment that movably attaches to the extendable multiwalled nanotube to the other of the two ends.

7. A method for tunably resonating a multiwalled nanotube, comprising:
   a) disposing an extendable mount attaching to at least one end of a multiwalled nanotube;
   b) displacing the extendable mount to extend the attached multiwalled nanotube to a desired displacement; and
   c) exciting the multiwalled nanotube to cause it to vibrate.

8. The method of claim 7 further comprising:
   a) detecting an amplitude of the vibration in the multiwalled nanotube.

9. The method of claim 7 wherein said multiwalled nanotube is a carbon multiwalled nanotube.

10. The method of claim 7, wherein the exciting step comprises:
    a) passing a current through the multiwalled nanotube; and
    b) providing an electromagnetic field located about the multiwalled nanotube.

11. The method of claim 10, further comprising:
    a) controlling the desired displacement so that the amplitude of the vibration of the multiwalled nanotube is maximized at a central resonant frequency; and
    b) measuring a frequency of the vibration of the multiwalled nanotube.

12. The method of claim 11, further comprising:
    a) reducing a particle number density of a dissipative fluid disposed about the multiwalled nanotube to increase a quality factor Q of the multiwalled nanotube.

13. The method of claim 11, further comprising:
    a) calculating a change in length of the multiwalled nanotube through a change in the central resonant frequency between a first and second value of the desired displacement.

* * * * *